(12) United States Patent
Kester

(10) Patent No.: US 6,682,545 B1
(45) Date of Patent: Jan. 27, 2004

(54) SYSTEM AND DEVICE FOR PREVENTING RESTENOSIS IN BODY VESSELS

(75) Inventor: Mark Kester, Harrisburg, PA (US)

(73) Assignee: The Penn State Research Foundation, University Park, PA (US)

( * ) Notice: Subject to any disclaimer, the term of this patent is extended or adjusted under 35 U.S.C. 154(b) by 354 days.

(21) Appl. No.: 09/679,715

(22) Filed: Oct. 5, 2000

Related U.S. Application Data

(60) Provisional application No. 60/157,960, filed on Oct. 6, 1999.

(51) Int. Cl.[7] ............................................. A61M 29/00
(52) U.S. Cl. ...................... 606/191; 606/194; 623/1.42; 623/1.46; 604/28; 604/103.01; 604/103.02
(58) Field of Search ................. 606/191, 108, 606/192, 194; 623/1.42, 1.46; 604/103.01, 103.02, 891.1, 28, 265, 266

(56) References Cited

U.S. PATENT DOCUMENTS

| | | | |
|---|---|---|---|
| 4,768,507 A | | 9/1988 | Fischell et al. ............. 128/303 |
| 5,061,267 A | | 10/1991 | Zeiher ........................ 606/40 |
| 5,102,402 A | * | 4/1992 | Dror et al. ............. 604/103.02 |
| 5,304,121 A | * | 4/1994 | Sahatjian ............... 604/103.02 |
| 5,324,261 A | * | 6/1994 | Amundson et al. .... 604/103.02 |
| 5,498,238 A | * | 3/1996 | Shapland et al. ....... 604/103.01 |
| 5,509,899 A | | 4/1996 | Fan et al. ..................... 604/96 |
| 5,545,208 A | * | 8/1996 | Wolff et al. .............. 604/891.1 |
| 5,562,922 A | * | 10/1996 | Lambert ..................... 424/427 |
| 5,599,307 A | | 2/1997 | Bacher et al. .............. 604/101 |
| 5,628,730 A | | 5/1997 | Shapland et al. ............. 604/21 |
| 5,634,901 A | | 6/1997 | Alba et al. ................... 604/96 |
| 5,674,192 A | * | 10/1997 | Sahatjian et al. ............. 604/28 |
| 5,679,400 A | * | 10/1997 | Tuch ......................... 427/2.14 |
| 5,681,589 A | * | 10/1997 | Wei et al. ................... 424/450 |
| 5,707,385 A | * | 1/1998 | Williams .................... 604/104 |
| 5,749,915 A | * | 5/1998 | Slepian ....................... 128/898 |
| 5,830,430 A | * | 11/1998 | Unger et al. ............... 424/1.21 |
| 5,833,651 A | * | 11/1998 | Donovan et al. ........... 604/265 |
| 5,947,889 A | | 9/1999 | Hehrlein ........................ 600/3 |
| 6,087,325 A | * | 7/2000 | Meers et al. ................ 424/450 |
| 6,143,276 A | * | 11/2000 | Unger ........................ 424/450 |
| 6,280,411 B1 | * | 8/2001 | Lennox ................. 604/103.01 |
| 6,299,604 B1 | * | 10/2001 | Ragheb et al. .............. 604/265 |

* cited by examiner

*Primary Examiner*—Rodney M. Lindsey
(74) *Attorney, Agent, or Firm*—Knobbe, Martens, Olson & Bear, LLP

(57) ABSTRACT

The present invention relates to a system and device for preventing stenosis and/or restenosis after an invasive procedure in a body vessel or cavity having an inner wall surface, the system comprising inserting a device coated with a growth arresting, lipid-derived, bioactive substance at a desired location along the inner wall surface of the body vessel or cavity.

16 Claims, 9 Drawing Sheets

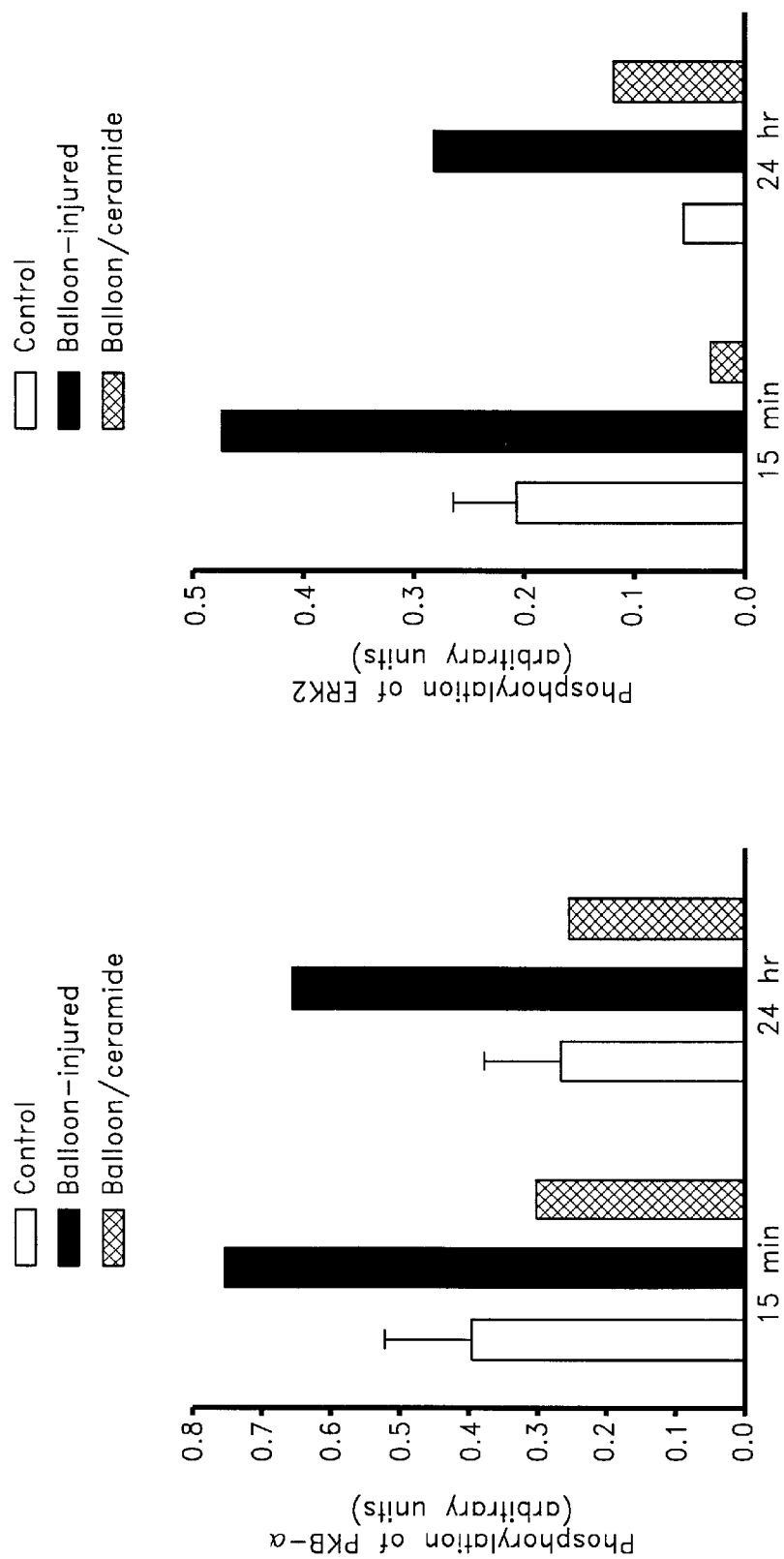

SYSTEM AND DEVICE FOR PREVENTING RESTENOSIS IN BODY VESSELS

This application claims priority to the U.S. provisional application No. 60/157,960 filed Oct. 6, 1999, now abandoned, which is incorporated herein by reference in its entirety.

BACKGROUND OF THE INVENTION

Restenosis persists as a major complication in the maintenance of vessel patency after percutaneous transluminal angioplasty in coronary (PTCA) and other vessels. Restenosis is a consequence of multiple factors, including vessel recoil, negative vascular remodeling, residual plaque burden, and neointimal hyperplasia. Neointimal hyperplasia reflects the migration and proliferation of vascular smooth muscle (VSM) cells with subsequent deposition of extracellular matrix components at the site of injury. Considerable evidence indicates that, in restenosis, growth factors stimulate the VSM cells to proliferate, resulting in a thickening of the tunica intima. Nearly 40% of all patients develop significant luminal narrowing within 6 months after angioplasty procedures. Consequently, despite the initial therapeutic benefits of angioplasty, within a few months after surgery, blood flow through the affected vessels can again become compromised. Conventional therapies, which include angiotensin-converting enzyme inhibitors, anticoagulants, and statins, are ineffective in preventing or reducing neointimal hyperplasia after stretch injury. Endovascular radiation therapy has shown some success in both animal and human trials, yet the long-term deleterious effects of this therapy on the artery have not been adequately evaluated.

Ceramide is a growth arresting metabolite of sphingomyelin, a major lipid component of the cell membrane. More specifically, ceramide is a complex lipid which can be found in the plasma membrane. It is produced by the breakdown of sphingomyelin by sphingomyelinases, a process which is enhanced during inflammatory cytokine (IL-1, TNF and CD 95 ligand) induced growth arrest and/or cell death. It appears that ceramide acts as a bioactive which can mediate vascular smooth muscle-growth arrest and/or apoptosis by the direct activation of certain kinases. It is hypothesized that direct and immediate delivery of a cell-permeable ceramide or analog via the balloon tip of an embolectomy catheter or chronic delivery via coating of a stent would reduce the VSM proliferation that is observed in restenosis after angioplasty.

It is known that ceramide inhibits VSM proliferation by activating c-jun N-terminal kinase (JNK) while suppressing extracellular signal regulated kinase (ERK) and protein kinase B (PKB) in vitro. Yet, the possibility that a cell-permeable ceramide could diminish VSM proliferation in vivo has until now not been tested. The use of catheters to open diseased arteries, body vessels or cavities is also known, as in e.g., U.S. Pat. No. 5,599,307, herein incorporated by reference. However, the prior art therapeutic devices themselves induce a significant amount of regrowth of VSM in the artery, which leads to secondary blockages or occlusions (i.e., restenosis).

SUMMARY OF THE INVENTION

The present invention relates to a system and device for preventing stenosis (narrowing) and/or restenosis (renarrowing) after an invasive procedure (e.g., vascular or surgical intervention) in a body vessel or cavity having an inner wall surface, the system comprising inserting a device coated with a growth-arresting, lipid derived, bioactive substance at a desired location along the inner wall surface of the body vessel or cavity. By delivering the substance directly and immediately to the site of action, subsequent regrowth of smooth muscle cells is prevented, thus overcoming the inflammatory response which occurs due to the body's dealing with the original surgical intervention, e.g., angioplasty.

In a preferred embodiment, the present invention discloses a ceramide treatment which significantly reduces neointimal hyperplasia induced by balloon angioplasty in carotid arteries. It is demonstrated that ceramide ameliorates stenosis by decreasing the trauma-associated phosphorylation of extracellular signal regulated kinase (ERK) and protein kinase B (PKB). As described below, it has been demonstrated that the utility of cell-permeable ceramide is a novel therapy for reducing restenosis after balloon angioplasty.

BRIEF DESCRIPTION OF THE DRAWINGS

FIGS. 5A–5C show the evidence from in vitro studies that ceramide arrests cell growth.

DETAILED DESCRIPTION OF THE INVENTION

Figure 1:
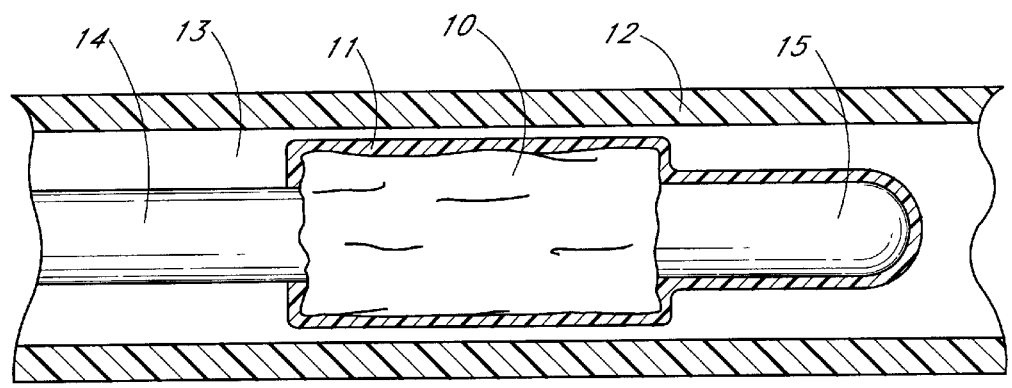
FIG. 1 is a cross-sectional view of a balloon catheter coated with the growth arresting lipid-derived bioactive substance.

The present invention relates to a system and device for preventing stenosis and/or restenosis after an invasive procedure in a body vessel or cavity having an inner wall surface, the system comprising inserting a device coated with a growth arresting, lipid-derived, bioactive substance at a desired location along the inner wall surface of the body vessel or cavity. By delivering the substance directly and immediately to the site of action, subsequent regrowth of smooth muscle cells is prevented, thus overcoming the inflammatory response which occurs due to the body's dealing with the original surgical intervention, e.g., angioplasty. The devices which may be enhanced with the treatment of the present invention include, but are not limited to, simple catheter/simple (one) balloon designs, a dual balloon catheter design, or stents. Microporous catheter design, infusion catheter design, rotary atherectomy device design, polymeric (e.g., polyacrylic acid) coated balloon designs, bioabsorbable coating designs, stent covers and perivascular matrices may all possibly be enhanced as well.

By "growth arresting," it is meant that the cells (e.g., vascular smooth muscle cells) are no longer responsive to growth factors or cytokines released from damaged tissue. By "lipid-derived," it is meant that the substances are for the metabolism of lipids in membranes. Therefore, there is minimal immunologic/inflammatory response of the body to these compounds. Finally, by "bioactive," it is meant that the agents transduce information from the outside membranes of the cell to the nucleus where new genes are activated or inactivated to change the phenotype of the cell. Examples of such antimitogenic materials include ceramides and ceramide derivatives, e.g., cell-permeable analogs and forms which are subject to diminished metabolism. These include, but are not limited to, derivatives of the SN-1 position including 1-chloro and 1-benzoyl ceramides, which would not be subject to phosphorylation at this position, as well as derivatives at the SN-2 position (amide linkage), such as a methylcarbamate group or a 2-0-ethyl substituent, which would not be subject to degradation by ceramidases. In addition, cell-permeable forms of these ceramide analogs can be utilized. Examples of these cell-permeable ceramides and/or derivatives contain 2–10 carbons and have short-chain fatty acids at the SN-2 position (C6 ceramide).

Other examples of growth arresting, lipid-derived, bioactive substances include, but are not limited to, dimethyl sphingosine, ether-linked diglycerides, ether-linked phosphatidic acids, and sphinganines.

The device to be coated is preferably dipped in a vehicle including DMSO/ethanol, the actual coating process performed in a sterile environment so as to result in an effective amount of coating material remaining on the device. Devices can then be subjected to radiation sterilization Ceramide-coated devices may be optimized for delivery from hydrophobic and hydrophilic coatings, as well as absorbable or polymeric matrices.

As shown in FIG. 1, which displays an embodiment containing a catheter and single balloon design, catheter 14 with associated balloon 10 is inserted into lumen 13, surrounded by artery wall 12. Catheter tip 15 and balloon 10 are coated with the growth arresting, lipid-derived bioactive substance 11 for use during a particular treatment, leading to opening of clogged and/or narrowed vessels that impede blood flow.

In a further preferred embodiment, the present invention relates to balloon catheters and/or stents coated with growth arresting, lipid-derived, bioactive substances and a system for preventing restenosis after an invasive procedure in a body vessel or cavity having an inner wall surface, the system comprising the steps of:

(a) inserting a therapeutic device (e.g., balloon on an embolectomy catheter, stent, and/or rotary atherectomy device) to reduce the narrowing of arteries in a desired location along the inner wall surface, the device coated with a growth arresting, lipid-derived, bioactive substance or derivative thereof;

(b) inflating the balloon on the embolectomy catheter or placing the stent in a portion of the vessel or cavity with damaged or diseased tissue;

(c) (i) supplying material (directly and immediately by inflation of the balloon, or at a sustained rate via the stent) to and (ii) removing plaque or debris from the diseased portion and/or serving as a scaffolding device; and (d) providing a treatment to the diseased or occluded portion of the vessel or cavity. Such steps will prevent secondary regrowth of the damaged vascular smooth muscle tissue, while still allowing wound healing.

Figure 2A:
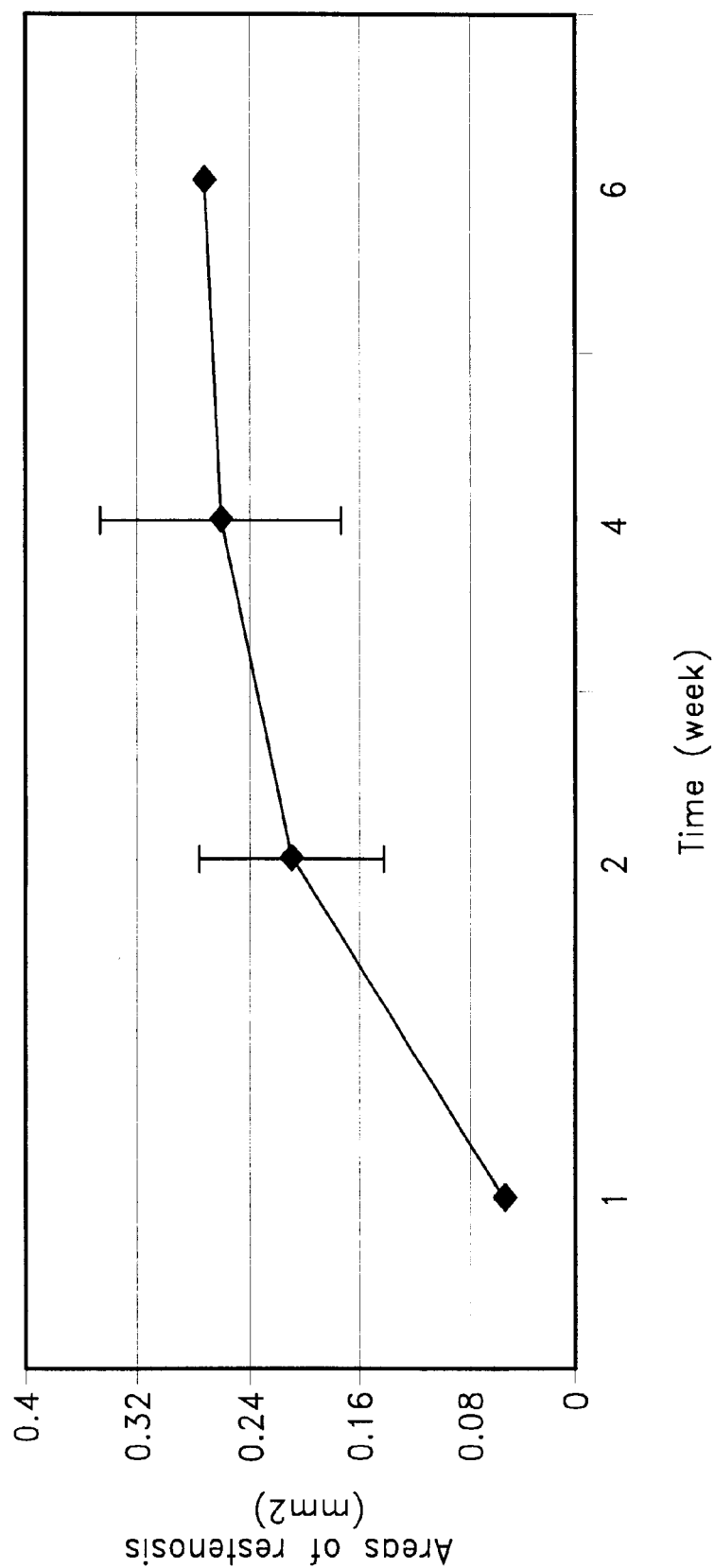
FIGS. 2A–2F are results of experiments evaluating the therapeutic potential of ceramide-coated embolectomy catheters upon restenosis after balloon angioplasty.
Figure 2B:
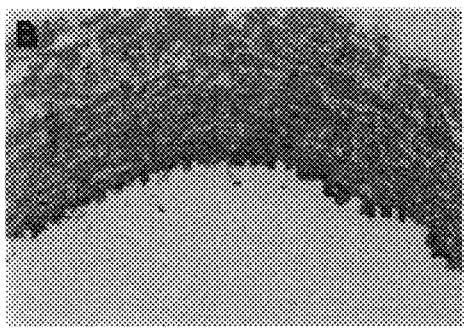
Figure 2C:
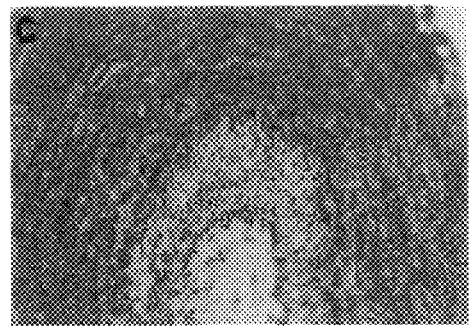
Figure 2D:
Figure 2E:
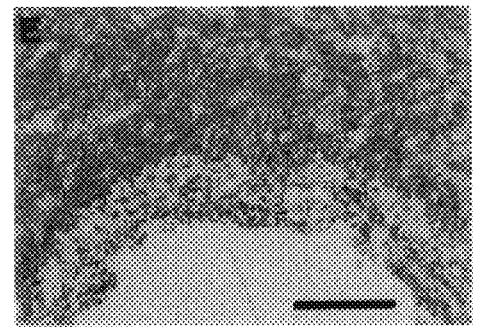
Figure 2F:
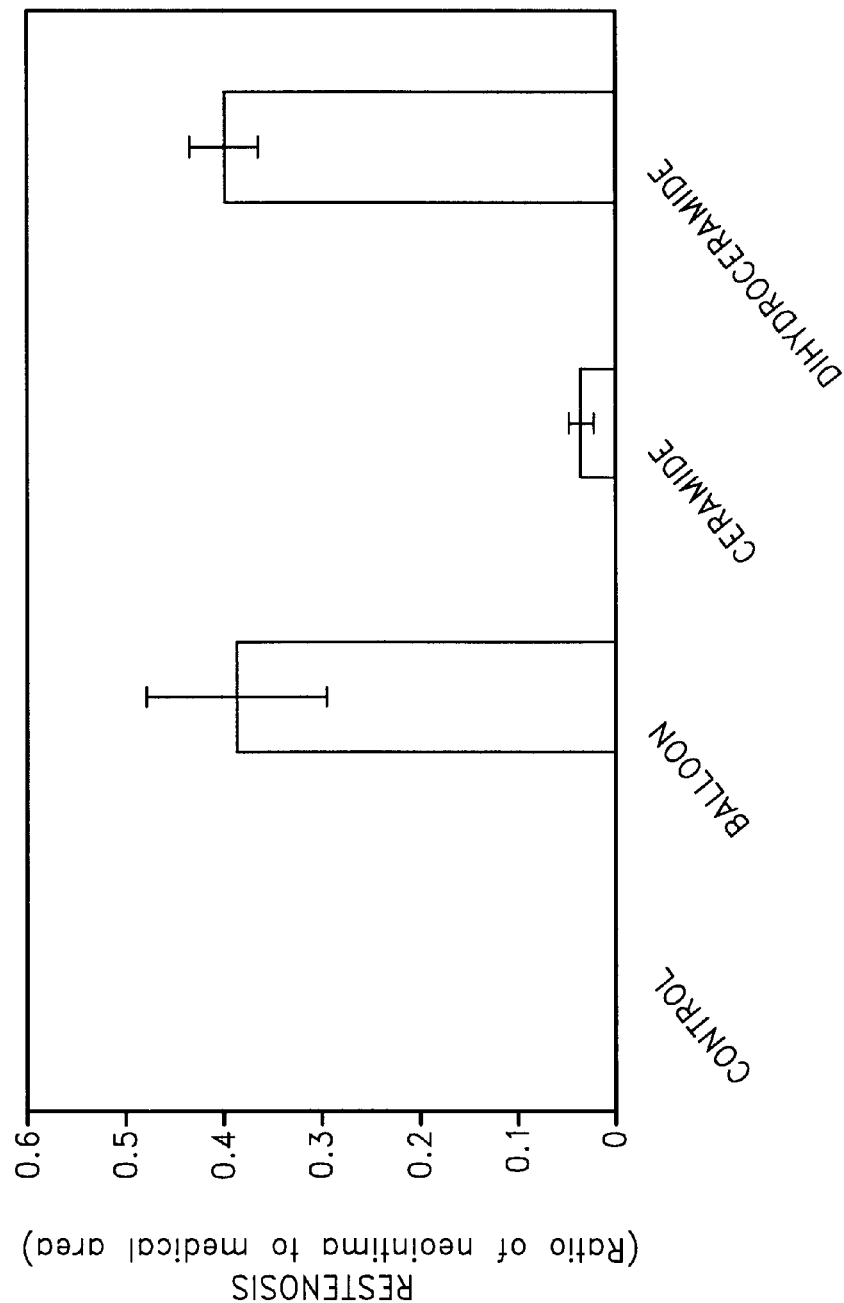

Experiments were designed to evaluate the therapeutic potential of ceramide-coated embolectomy catheters upon restenosis after balloon angioplasty. Initial studies assessed the extent of restenosis in rabbit carotid arteries after balloon angioplasty as a function of time. Animals were sacrificed 1, 2, 4 and 6 weeks after balloon injury. Marked neointimal hyperplasia was observed as early as 1 week and peaked at 4 weeks (FIG. 2A). Sham-treated carotid arteries showed no signs of neointimal hyperplasia at any time. The medial vascular smooth muscle layer also showed distinct hypertrophic injury after balloon treatment. Based upon these results, the effects of ceramide upon dynamic restenotic VSM growth, 2 weeks post balloon injury were investigated. FIGS. 2B–E illustrate hematoxylin and eosin stained cryostat sections of rabbit carotid arteries. In addition to the sham-treated control artery (FIG. 2B), the three treatment groups included a vehicle-treated balloon (FIG. 2C), a $C_6$-ceramide-coated balloon (FIG. 2D) and a dihydro-$C_6$-ceramide(an inactive, inert substance)-coated balloon (FIG. 2E). Surprisingly, the $C_6$-ceramide treatment significantly reduced the neointimal hyperplasia induced by balloon angioplasty. A quantitative analysis revealed that ceramide inhibited the balloon-induced neointimal formation by 92% as reflected in the reduction of the neointimal/medial ratio (FIG. 2F). In contrast, dihydro-$C_6$-ceramide, an inactive analogue of C6-ceramide, did not reduce restenosis after balloon injury. Thus, the inhibitory effect requires bioactive ceramide and cannot be duplicated using structurally similar but inactive lipids. Furthermore, it may be theorized that the effects of ceramide are due to biochemical actions and not lipophilic properties.

Specifically, in FIG. 2, $C_6$-ceramide but not dihydro-$CC_6$-ceramide blocked neointimal hyperplasia after balloon angioplasty in rabbit carotid arteries. Initial experiments optimized the methods to induce restenosis after angioplasty in carotid arteries from New Zealand white rabbits. Twenty-one rabbits were divided into three experimental groups, undergoing either balloon angioplasty with a vehicle-treated catheter, a $C_6$-ceramide-treated catheter or a dihydro-$C_6$-ceramide-treated catheter. Each rabbit underwent identical procedures to denude the common carotid artery of endothelium and establish the cellular conditions to promote restenosis. The right common carotid served as the sham control while the left carotid served as the experimental side. There were no significant differences between sham control, vehicle control or ceramide-treated arteries in terms of either tissue wet weight or cellular protein content. FIG. 2A represents the time course of restenosis after angioplasty while FIGS. 2B–2E depict representative H/E stained sections. The upper left panel (FIG. 2B) depicts a sham-treated control artery while the upper right panel (FIG. 2C) shows an artery treated with a DMSO/ethanol (1:1,v/v)-coated balloon. The bottom left panel (FIG. 2D) shows an artery treated with a $C_6$-ceramide-coated balloon and the bottom right panel (FIG. 2E) an artery treated with dihydro-$C_6$-ceramide, a biologically inactive form of ceramide. The scale for these photomicrographs is 200 microns. FIG. 2F quantifies the extent of restenotic lesions.

Figure 3A:
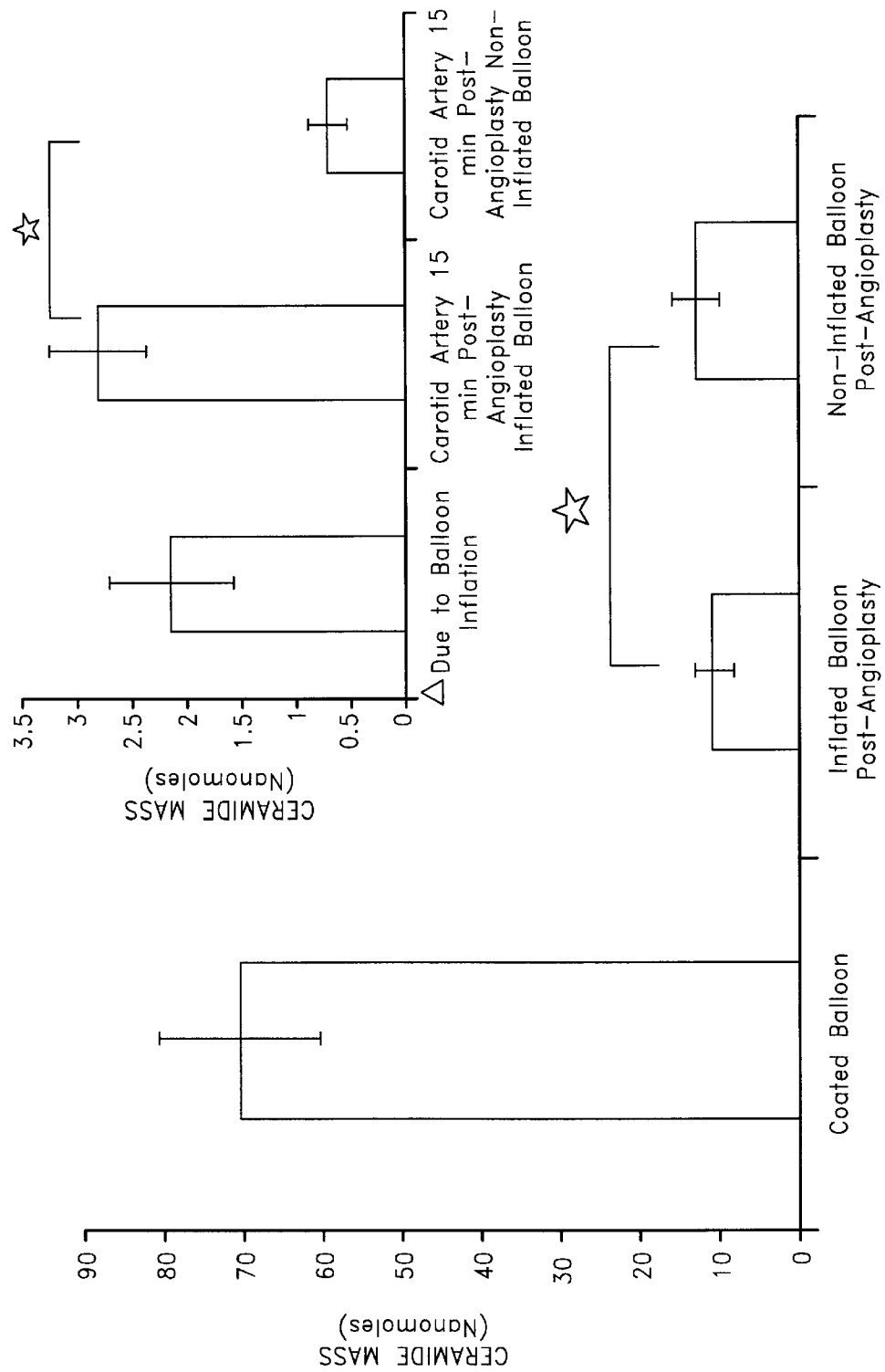
FIGS. 3A–3D show results of experiments conducted to quantify ceramide transfer between the balloon and the carotid artery.

The inability of experimentally effective therapies to succeed in clinical trials is often the consequence of suboptimal doses of therapeutics being delivered to the site of injury for the appropriate duration. Moreover, the efficacy of therapy may be a consequence of biomechanical force transferring ceramide from the inflated balloon to the site of vascular lesions. Therefore, experiments were conducted to quantify ceramide transfer between the balloon and the carotid artery; the pharmacokinetics of ceramide transfer and delivery from the balloon catheter to the damaged artery was assessed. Using [$^3$H]$C_6$-ceramide as a tracer, it was calculated that 70±10 nmol of $C_6$-ceramide was applied to the balloon as a gel from a solution of 5 μmol of $C_6$-ceramide. FIG. 3A shows that, after insertion and inflation, 12±2 nmol remained on the balloon. This translates to roughly 58 nmol of $C_6$-ceramide being transferred from the balloon catheter during the angioplasty procedure. To test whether inflation of the balloon within the carotid artery was essential for optimal transfer of the ceramide, the surgical procedure was performed using noninflated balloons. The recovered ceramide mass on the inserted but noninflated balloon was 14±3 nmol. Rabbit carotid arteries treated with radiolabeled lipid were homogenized, and lipid products were separated by thin-layer chromatography (TLC) (FIG. 3A). The mass of intact ceramide isolated 15 minutes after angioplasty was 2.7±0.4 nmol for inflated balloon treatments and 0.7±0.2 nmol for noninflated balloon treatments. The amount of ceramide recovered from excised tissues did not differ significantly from the amount of ceramide transferred to the tissue as a consequence of balloon inflation. As the transferred ceramide was initially delivered to 0.0365 $cm^3$ of carotid artery luminal volume, the effective concentration of ceramide at the site of balloon injury is estimated to be 1.5 mmol/L. Thus, an effective and reproducible dose of ceramide can be delivered to the damaged artery as a consequence of the balloon inflation.

Figure 3B:
Figure 3C:
Figure 3D:
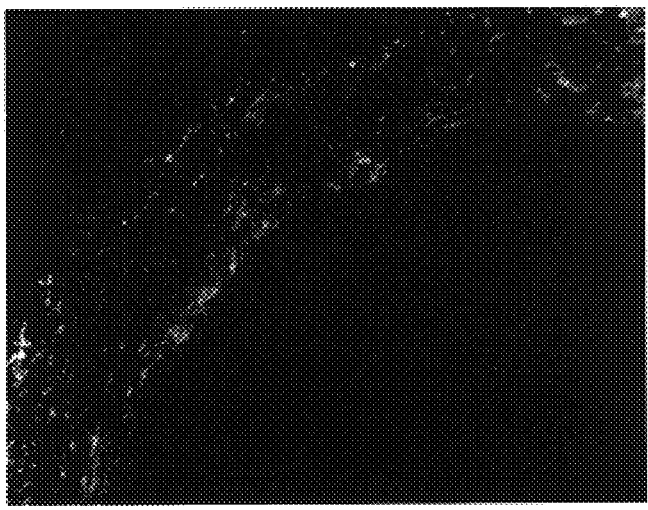

In situ autoradiography was utilized to document arterial penetrance for $[^3H]C_6$-ceramide transferred from the balloon catheter after angioplasty (FIGS. 3B through 3D). Compared with unlabeled arteries (panel B), $[^3H]C_6$-ceramide was observed throughout the medial layers of the artery 15 minutes after angioplasty (panel C). This increase in pixel intensity reflects an increase in intact ceramide, as at this time point 89±4% of the radiolabel comigrates with authentic $C_6$-ceramide standards. Pixel intensity was more intense in inflated (panel C) versus noninflated (panel D) arteries. Expressed as pixel density per square millimeter for 10 randomly selected blocks with background values subtracted, medial staining was increased 4.7±0.2-fold for ceramide-coated inflated versus noninflated balloons. Again, this supports the conclusion that balloon inflation leads to maximal delivery and penetrance. Thus, a lipid-coated balloon delivers a therapeutic dose of ceramide to tissues underlying the site of vascular stretch injury, and demonstrates that a short-term application of cell-permeable ceramide is sufficient to completely penetrate injured arteries and to reduce intimal proliferation despite an inflammatory milieu.

The degradation of the rapidly intercalated radiolabeled ceramide by TLC was also assessed. For the 15-minute postangioplasty time point, 89±4% of the TLC-separated lipid comigrated with authentic $C_6$-ceramide standards. This corresponded to a recovered mass of 2.7±0.4 nmol of ceramide. At 60 minutes after angioplasty, 1.3±0.6 nmol of ceramide was recovered. Thus, 50% radiolabel can still be recovered as intact ceramide in 1 hour. This decrease in ceramide mass corresponded to an increase in TLC-separated gangliosides and cerebrosides but not sphingosines.

It is noted that infusion-type catheters have the advantage to deliver ceramide in a BSA vehicle at a discrete dose to the site of arterial injury. It was thus determined whether ceramide delivered by solution using an infusion-type catheter is also effective in reducing restenosis as ceramide delivered using a catheter with a gel coated balloon tip. The balloon at the tip of a 4F arterial bilumen irrigation embolectomy catheter was inflated to a diameter equivalent to that of the earlier experiments. Three infusions of 10 $\mu$M $C_6$-ceramide for 1 minute each reduced restenosis after balloon angioplasty by 39%. Dihydro-$C_6$-ceramide at an equivalent dose had no effect upon restenotic lesions. These studies further support the novelty and efficacy of ceramide-coated balloon catheters as intra-arterial site-specific delivery devices.

To prevent thrombus formation, patients routinely receive anti-coagulants prior to percutaneous transluminal coronary angioplasty. Thus, the consequences of anticoagulation therapy on the effectiveness of ceramide therapy were investigated. Neither ceramide- nor vehicle-treated balloon angioplasty induced thrombus formation. Lovenox (a low molecular weight heparin), administered subcutaneously (2.5 mg/kg) for 7 days post-surgery, did not by itself diminish restenosis and did not augment ceramide-induced inhibition of restenosis, suggesting that ceramide treatment is equally effective in both anti-coagulated and untreated protocols.

Figure 4A:
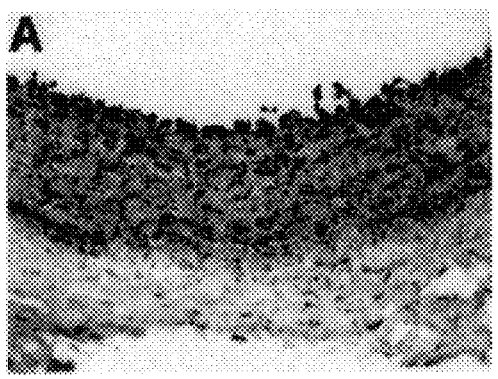
FIGS. 4A–4F show the effects of ceramide treatment upon VSM cell growth.
Figure 4B:
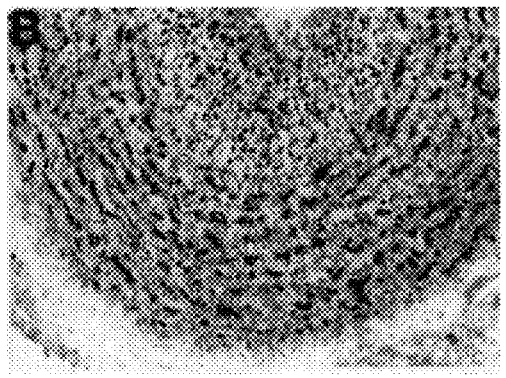
Figure 4C:
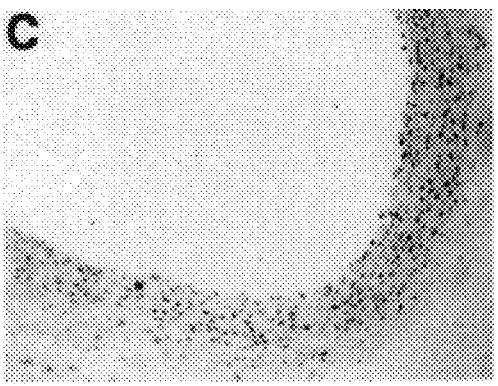
Figure 4D:
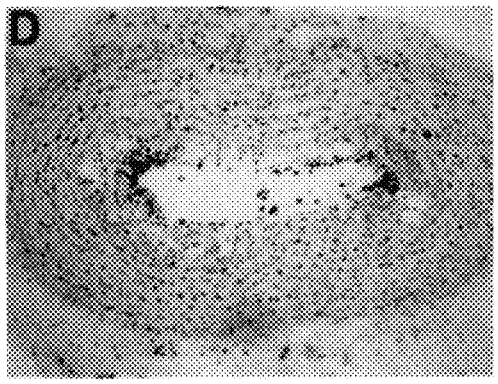
Figure 4E:
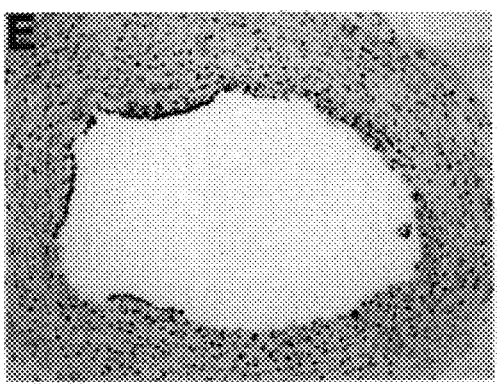
Figure 4F:
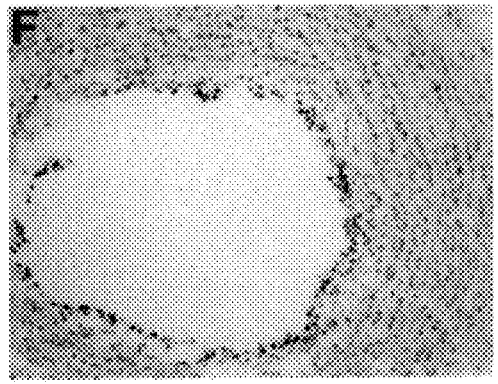

The effects of ceramide treatment upon VSM cell growth in vivo were also investigated. Imunohistochemical techniques were employed to identify VSM using smooth muscle cell-specific actin antibody (FIGS. 4A–B) and cell growth using proliferating cell nuclear antigen (PCNA) antibody (FIGS. 4C–F). The positive staining with the actin antibody indicates that VSM was a major component of balloon injury-induced neointimal formation (FIG. 4B). Also, this photomicrograph shows dramatic balloon angioplasty-induced ruffling and dispersion of VSM in the medial layer. PCNA is synthesized in early G1 and S phases of the cell cycle, and thus can be used as a marker for cell proliferation. In FIGS. 4C–F, representative photomicrographs depicting PCNA positive staining are shown for control, balloon-injured, ceramide-treated and dihydroceramide-treated carotid arteries, respectively. The percentage of PCNA positive cells in balloon-injured arteries (2.8%±0.1%) was dramatically increased compared with control vessels (0.2%±0.1%). $C_6$-ceramide (0.6%±0.2%) but not dihydro-$C_6$-ceramide (1.9%±0.3%) diminished the number of PCNA positive cells in the neointimal layer but not in the medial layer of the carotid artery. These data demonstrate that ceramide reduces neointimal hyperplasia by diminishing the percentage of VSM that enters the cell cycle after trauma to the vessel wall.

Specifically, in FIG. 4, ceramide-treated catheters reduced PCNA expression in vascular smooth muscle cells after angioplasty. Smooth muscle actin expression was analyzed by immunohistochemistry utilizing a monoclonal anti-alpha smooth muscle antibody, and PCNA positive cell numbers were assessed with a primary mouse monoclonal IgG2a antibody for PCNA. Stain control slides substituted the primary antibody with nonspecific mouse IgG and did not reveal any specific or selective staining. These immunohistochemical micrographs are representative of four separate experiments. Panels A–B reflect smooth muscle actin staining for control and balloon-injured arteries, respectively while panels C–F represent PCNA staining for control, balloon-injured, ceramide-coated balloon-injured and dihydro-ceramide-coated balloon-injured carotid arteries, respectively. The scale for these photomicrographs is 200 microns.

Figure 5A:
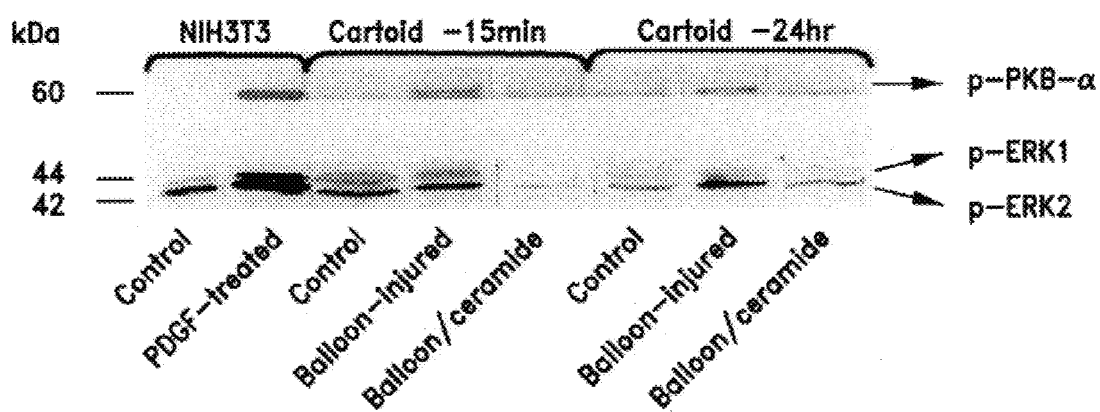

Evidence from in vitro studies shows that ceramide arrests cell growth by inhibiting the growth factor-induced extra-cellular signal regulated kinase (ERK) cascade and possibly by inhibiting the protein kinase B (PKB) cascade. Thus, to elucidate mechanisms by which ceramide prevents restenosis, the phosphorylation states of ERK2 and PKB$\alpha$ were investigated using freshly excised carotid arteries after angioplasty (FIG. 5). Phosphorylation of ERK2 and PKB$\alpha$ were increased at 15 minutes and 24 hours post-balloon injury. The sustained phosphorylation of these kinases most likely reflects continuous remodeling of damaged arteries. Immediately after ceramide treatment, the phosphorylation states of these kinases were reduced below basal activation levels. Thus, acute ceramide therapy may directly modulate kinases or regulate putative ceramide-activated protein phosphatases that down-regulate these signaling pathways.

Specifically, in FIG. 5, ERK2 and PKBα phosphorylation was diminished after ceramide-coated balloon angioplasty in rabbit carotid arteries. Panel A depicts a representative Western blot for ERK-2 and PKBα probed using phosphorylation-specific antibodies. Lysates from NIH3T3 cells treated with or without PDGF were used as positive and negative controls, respectively. This immunoblot is representative of similar experiments using a total of 8 animals. Panels B–C quantifies the immunoblot data.

It has been previously demonstrated that $C_6$-ceramide mimicked the effect of IL-1 to inhibit both tyrosine kinase receptor- and G-protein receptor-linked mitogenesis in A7r5 aortic smooth muscle cells and rat glomerular mesangial cells. Ceramide treatment correlated with growth arrest at $G_0G_1$ and not apoptosis in these smooth muscle-like pericytes. The present invention shows that $C_6$-ceramide does not induce significant apoptosis in primary VSM isolated from rabbit carotid arteries as assessed by fluorescence-activated cell sorting after propidium iodide staining using a previously described doublet discrimination protocol. Specifically, primary rabbit VSM treated with 5 μM $C_6$-ceramide or dihydro-$C_6$-ceramide for either 24 or 40 hours showed less than 1% apoptotic cell death. As a control, okadaic acid treatment (100 nM) significantly induced apoptosis after 24 hours (52%) and 40 hours (69%±2%). Thus, the therapeutic efficacy of cell-perneable ceramide in restenosis includes its ability to arrest VSM growth without inducing significant apoptosis.

Other cell-permeable ceramide derivatives can also limit neointimal hyperplasia. Derivatives of ceramide, in which the amide-linked fatty acyl chain is replaced with dimethyl moieties, e.g., dimethylsphingosine, are also effective in limiting angioplasty-induced injury.

Although altered ceramide metabolism has been implicated in atherosclerosis, diabetes mellitus and cancer, ceramide analogues have not yet been considered as therapeutics for proliferative vascular diseases. Increased concentrations of lactosyl- and glyco-ceramide conjugates at the expense of endogenous ceramide were noted in models of atherosclerosis and diabetes mellitus, and this diminished level of ceramide correlated with VSM proliferation and vasoconstriction. With endogenous levels of ceramide depleted, it is logical to consider the use of exogenous ceramide analogues as antimitogenic agents. The present invention demonstrates that ceramide is a strong candidate for preventing restenosis after angioplasty. The present invention is also anticipated to be effective in treating stenosis of e.g., coronary, renal and femoral arteries, and may have venuous uses as well, e.g., as a calibrated portal caval shunting or unclogging blocked saphenous veins used for coronary bypass. Furthermore, the present invention may have uses in such areas as diabetic retinopathy, where smooth muscle-like cells are activated and proliferate in front of the retina, resulting in blindness. Locally delivered ceramide can also be used to potentially treat dysregulated smooth muscle growth in stenosis of vascular access lines after chronic dialysis. In addition to delivering these drugs on the tips of balloon catheters, through infusion ports, or coated on stents, these antimitogenic sphingolipid derivatives can be delivered as components of conventional or cationic liposomal vectors, potentially augmenting the efficacy of gene transfer and targeting strategies.

Thus, the present invention demonstrates inhibition of smooth muscle cell growth at the site of injury, when ceramide or other growth arresting, lipid-derived derivatives are locally administered by coating balloons and stents. In addition, ceramides or other growth arresting, lipid-derived, bioactive substances can be delivered at fixed dosages via infusion or microporous catheter designs. Infusion catheters deliver the substance through a port distal to the inflated balloon. Microporous catheters deliver the substance via minute pores on the balloon surface. Also, the materials of the present invention can be delivered via a double balloon, infusion port, catheter design to deliver substance to the damaged arterial wall, isolated between the two inflated balloons. According to a preferred embodiment of the present invention, $C_6$-ceramide, a cell permeable ceramide, inhibits smooth muscle cell proliferation at the angioplasty site. Alternatively, other cell-permeable ceramide derivatives can also limit neointimal hyperplasia. Derivatives of ceramide, in which the amide-linked fatty acyl chain is replaced with dimethyl moieties, are also effective in limiting angioplasty-induced injury.

I claim:

1. A method for preventing restenosis after an invasive procedure in a body vessel or cavity having an inner wall surface, said method comprising:

inserting a device along the inner wall surface of the body vessel or cavity, said device combined with a growth-arresting, lipid-derived bioactive compound selected from the group consisting of ceramide or derivatives thereof, dimethyl sphingosine, ether-linked diglycerides, ether-linked phosphatidic acids and sphinganines; and delivering said growth-arresting, lipid-derived bioactive compound to the inner wall surface.

2. The method as recited in claim 1, wherein said device is a catheter, a balloon catheter, and/or a stent.

3. The method of claim 1, wherein said growth-arresting, lipid-derived bioactive compound is coated onto said device.

4. The method of claim 1, wherein said body vessel is a blood vessel.

5. The method as recited in claim 1, wherein said growth-arresting, lipid-derived bioactive compound is ceramide or a derivative thereof, that contains a 2–10 carbon short-chain fatty acid at SN-2 position.

6. The method as recited in claim 5, wherein the ceramide or derivative thereof is a $C_6$-ceramide.

7. The method as recited in claim 1, wherein said growth-arresting, lipid-derived bioactive compound is delivered through an infusion port(s) of said device.

8. The method as recited in claim 1, wherein said growth-arresting, lipid-derived bioactive compound is delivered at a dose sufficient to reduce neointimal hyperplasia induced by said invasive procedure.

9. The method as recited in claim 8, wherein said growth-arresting, lipid-derived bioactive compound reduces neointimal hyperplasia by diminishing the percentage of vascular smooth muscle cells that are proliferating and/or migrating, without inducing significant apoptosis.

10. The method as recited in claim 8, wherein said growth-arresting, lipid-derived bioactive compound reduces neointimal hyperplasia by diminishing the percentage of vascular smooth muscle cells that enter the cell cycle.

11. A combination for preventing stenosis and restenosis in a body vessel or cavity having an inner wall surface, said combination comprising a device and a growth-arresting, lipid-derived, bioactive compound selected from the group consisting of ceramide or derivatives thereof, dimethyl sphingosine, ether-linked diglycerides, ether-linked phosphatidic acids and sphinganines.

12. The combination as recited in claim 11, wherein said growth-arresting, lipid-derived bioactive compound is ceramide or a derivative thereof, that contains a 2–10 carbon short-chain fatty acid at SN-2 position.

13. The combination as recited in claim 12, wherein the ceramide or derivative thereof is a $C_6$-ceramide.

14. The combination of claim 11, wherein said growth-arresting, lipid-derived bioactive compound is in solution.

15. The device of claim 14, further comprising a port(s) adapted for delivery of said growth-arresting, lipid-derived bioactive compound in solution via systemic infusion.

16. The combination of claim 11, wherein said growth-arresting, lipid-derived bioactive compound is coated onto said device.

* * * * *

UNITED STATES PATENT AND TRADEMARK OFFICE
CERTIFICATE OF CORRECTION

PATENT NO. : 6,682,545 B1
DATED : January 27, 2004
INVENTOR(S) : Mark Kester

It is certified that error appears in the above-identified patent and that said Letters Patent is hereby corrected as shown below:

Column 10,
Line 1, please delete "The device" and insert therefore, -- The combination --.

Signed and Sealed this

Eighteenth Day of January, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,682,545 B1 | Page 1 of 1 |
| APPLICATION NO. | : 09/679,715 | |
| DATED | : January 27, 2004 | |
| INVENTOR(S) | : Mark Kester | |

It is certified that error appears in the above-identified patent and that said Letters Patent is hereby corrected as shown below:

Please add the following header and paragraph immediately after the Title of the Invention:

STATEMENT REGARDING FEDERALLY SPONSORED R&D

This invention was made with support from the Government of the United States of America under NIH Grant No. 5 R01 DK53715. The Government has certain rights in the invention.

Column 10,
Line 1, please delete "The device" and insert therefore, -- The combination --.

Signed and Sealed this

First Day of July, 2008

JON W. DUDAS
*Director of the United States Patent and Trademark Office*